(12) United States Patent
Kozyuk et al.

(10) Patent No.: US 9,701,922 B2
(45) Date of Patent: *Jul. 11, 2017

(54) METHOD FOR ENHANCING OIL PRODUCTION FROM GRAIN

(71) Applicant: Arisdyne Systems, Inc., Cleveland, OH (US)

(72) Inventors: Oleg Kozyuk, North Ridgeville, OH (US); Peter Reimers, Shaker Heights, OH (US)

(73) Assignee: ARISDYNE SYSTEMS, INC., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/350,267

(22) Filed: Nov. 14, 2016

(65) Prior Publication Data

US 2017/0058232 A1  Mar. 2, 2017

Related U.S. Application Data

(63) Continuation of application No. 14/039,483, filed on Sep. 27, 2013.

(51) Int. Cl.
| | |
|---|---|
| *C11B 1/10* | (2006.01) |
| *C11B 1/04* | (2006.01) |
| *C12P 19/04* | (2006.01) |
| *B01D 11/02* | (2006.01) |

(52) U.S. Cl.
CPC ............ *C11B 1/04* (2013.01); *B01D 11/0261* (2013.01); *C11B 1/10* (2013.01); *C12P 19/04* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 7,667,082 B2 | 2/2010 | Kozyuk | |
| 8,143,460 B2 | 3/2012 | Kozyuk | |
| 9,018,404 B2 * | 4/2015 | Brophy | C11B 1/106 422/255 |
| 2006/0041152 A1 * | 2/2006 | Cantrell | B01D 3/004 554/8 |
| 2011/0136194 A1 * | 6/2011 | Kozyuk | C12P 7/06 435/161 |
| 2012/0181216 A1 | 7/2012 | Kozyuk et al. | |
| 2013/0062249 A1 | 3/2013 | Kozyuk et al. | |
| 2013/0273627 A1 | 10/2013 | Kozyuk | |

OTHER PUBLICATIONS

Doris Kimbrough "Anytime Anywhere Chemistry Experience: Fermentation and Distillation" 8pgs 2000.*

* cited by examiner

*Primary Examiner* — Thane Underdahl
(74) *Attorney, Agent, or Firm* — Pearne & Gordon LLP

(57) ABSTRACT

A process for increasing oil yield from grain that includes passing a grain-based liquid stream of an alcohol production process through a cavitation apparatus to apply cavitational energy to the grain-based liquid stream, wherein the cavitational energy is applied to the grain-based liquid stream prior to a distillation phase of the alcohol production process.

9 Claims, 2 Drawing Sheets

METHOD FOR ENHANCING OIL PRODUCTION FROM GRAIN

FIELD

The invention relates to processes for producing oil from grain, and more particularly, processes for increasing oil yield by applying cavitational energy prior to distillation in an alcohol production process.

BACKGROUND

Alcohols are a renewable and clean fuel source. A grain alcohol commonly used as a fuel source is ethanol, which can be produced, in large part, from corn by the fermentation of starch. Generally, alcohol production is accomplished through a fermentation and distillation process wherein starches are released and converted to sugars, and then the sugars are converted to alcohol by the addition of yeast. At an industrial level, yeast fermentation processes only convert about one-third of the corn into alcohol.

In addition to producing alcohol, oil may be produced as a by-product to an alcohol production. Prior methods described methods teaching autoclaving stillage streams and extracting oil from ethanol. In addition, methods of processing post-fermentation thin stillage have been taught, but require multiple separation steps. Accordingly, there is a need to provide a more efficient and economical process to recover oil from a byproduct, such as thin stillage, created during a dry milling process for ethanol production.

SUMMARY

A method for enhancing oil production that includes providing a grain-based liquid stream of an alcohol production process prior to a distillation phase of the alcohol production process; passing the grain-based liquid stream through a cavitation apparatus at a differential processing pressure of at least 150 kPa to apply a cavitation energy to the grain-based liquid stream prior to an alcohol distillation phase of the process; and separating oil from stillage following the alcohol distillation phase of the alcohol production process.

A method for enhancing by-product oil yield in an alcohol production process by passing a grain-based liquid stream of the alcohol production process through a cavitation apparatus to apply a cavitation energy to the grain-based liquid stream, the cavitation activation energy being applied to the grain-based liquid stream prior to a fermentation phase of the alcohol production process.

DETAILED DESCRIPTION

Figure 1:
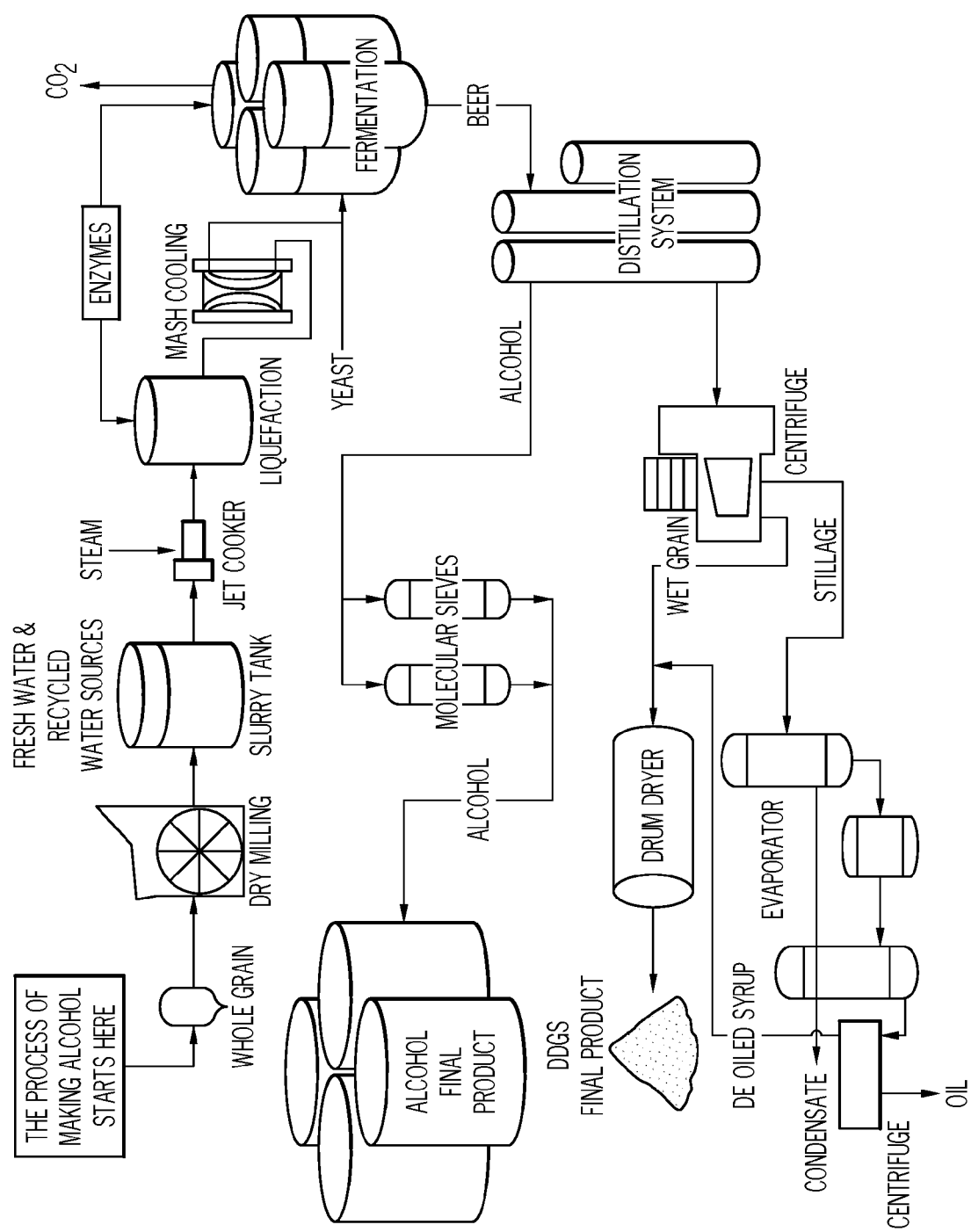
FIG. 1 is a process flow diagram of an alcohol production process and an oil by-product process.

Herein, when a range such as 5-25 (or 5 to 25) is given, this means preferably at least or more than 5 and, separately and independently, preferably not more than or less than 25. In an example, such a range defines independently not less than 5, and separately and independently, not more than 25.

Cavitation energy can be used to increase oil yield from an alcohol production process. When applied, cavitation energy can break or fracture protein and a fiber matrix contained in a grain-based liquid stream, which can allow entrapped oil to be released and more easily recovered downstream of a distillation phase. Preferably, cavitation energy is applied with the use of a cavitation apparatus located upstream of the distillation and/or fermentation phases of an alcohol production process.

Adding a cavitation step to the alcohol production process, wherein parameters such as pressure and temperature can be controlled, can increase oil yield by at least 10% as compared to oil yield from the same alcohol production process without cavitation energy being used, for example, cavitation energy being applied prior to the distillation phase of the alcohol production process. In general, cavitation can be described as a generation, subsequent growth and collapse, of cavitation bubbles and cavities. Energy is elastically stored in creating a cavitation activation energy bubble. When the cavitation activation energy bubble collapses, energy is released and generates very high temperatures, pressures, and shearing forces.

The cavitation bubbles contain mostly steam, although a level of steam fluctuates depending on a temperature at which the cavitation bubbles are formed. For instance, cavitation bubbles formed at lower temperatures contain less steam. Cavitation bubbles containing less steam will collapse more energetically and generate higher local temperatures and pressures. These higher temperatures and pressures can stimulate progress of structural separation of components and breakdown on chemical bonds that bind components that may not be possible under ordinary conditions, such as standard temperature and pressure (STP).

For example, cavitation energy can promote cellulose molecules to loosen, shake off, and/or strip away from lignin and protein components. In addition, the cavitation energy can destructure and disaggregate oils in the grain-based liquid stream, such as germ oil present in corn germ can, and the oils can be fully or partially liberated from corn germ during processing steps prior to a distillation process, such as liquefaction or mash cooling when enzymes are present in the grain-based liquid stream. Any oils or germ oil present can function as non-fermented/partially fermented, non-reactive, partially reactive de-foaming agent in a fermentation reactor with at least a portion of oils passing through the distillation process or phase into stillage, wherein stillage is whole stillage, thin stillage, inner evaporator effect thin stillage concentrate, or concentrated thin stillage syrups. The stillage can be further processed to separate the oils to enhance by-product oil yield in the alcohol production process as compared to not using such cavitational energy prior to the distillation phase.

Turning to the figures, FIG. 1 shows a starch to ethanol production process, wherein pipes, hoses, or other conventional industrial equipment can be used to facilitate the fluid communication of the elements and streams discussed herein. The production process begins when grain, such as whole kernel corn, is subject to a dry milling phase. The dry milling phase is used to grind the grain into meal or powder. For example, grains can include corn, rye, sorghum, wheat, beans, barley, oats, rice, or combinations thereof. As used herein, the term "grain" can comprise a whole grain or portions of the whole grain such as product from a dry-milling process used in an alcohol production process.

Grain can be mixed with water in a slurry tank to form a grain-based liquid stream, which can be in the form of a slurry. The slurry can further include other ingredients that are conventional in the alcohol production industry. The time in which the grain and water are mixed together is preferably in the range of 15 to 60 minutes, for example at least 15, 20, 30, 40, 50 or 60 minutes. The temperature at which the mixing will take place is preferably in the range of 20 to 85 degrees Celsius or about 40, 50, 60, 70, 75 or 80 degrees Celsius. The grain-based liquid stream can include at least 5, 10, 15, 20, 25, 30, 40, 50 or 60 weight percent grain, based on the total weight of the grain-based liquid stream. The remaining components of the grain-based can include entirely or essentially water, or other conventional additives.

After the grain-based liquid stream is formed in the slurry tank, the grain-based liquid stream can be heated in a cooking phase, such as with a jet cooker, to approximately 50 to 100 degrees Celsius. In the cooking or heating phase, the grain-based liquid stream can be held at an elevated temperature of approximately 80 to 100 degrees Celsius for a period of 4 to 8 hours. Temperature, pressure, and amount time elapsed may vary depending upon a specific application.

Following the cooking phase, enzymes, such as amylase, α-amylase, β-amylase, and γ-amylase, protease, cellulase, xylanases, ligninases enzymes or combinations thereof, can be added to the grain-based liquid stream, for example, in a liquefaction phase or downstream of the cooling phase but before fermentation as shown in FIG. 1. For instance, the enzymes, such as amylase, α-amylase, β-amylase, and γ-amylase, protease enzymes can be added to the grain-based liquid stream held in the liquefaction tank to promote breakdown of starch polymer into short sections, which can be maltodextrins and oligosaccharides. The grain-based liquid stream including the added enzymes can be held in the liquefaction tank for a period of time as known in the art. Following the liquefaction phase, additional enzymes, such as cellulase, xylanases, ligninases enzymes, can be added to the grain-based liquid stream in a mash cooling phase. A sugar mash is created in the grain-based liquid stream during the mash cooling phase.

After the cooling phase and generation of sugar mash in the grain-based liquid stream, the stream is sent to a fermentation phase. The sugar mash of the grain-based liquid stream will be transferred to fermentation containers or tanks wherein yeast can convert the sugar mash into carbon dioxide and alcohol, such as ethanol. Upon transfer of the sugar mash to the fermentation containers, additional enzymes, urea and yeast can be added to the sugar mash, which is left to ferment for a period of time, for example at least 40 to 80 hours, or about 60 hours. Resulting product from the fermentation containers is referred to as "beer" that contains alcohol and solids. These solids can be both soluble and insoluble, such as non-fermentable components left over from the grain. A distillation phase may follow the fermentation phase where alcohol is separated from a liquid carrier, such as water, and solids. The solids may contain stillage and non-fermentable compounds. The water can be recycled and used, for example, in the slurry tanks. The non-fermentable compounds may be separated from the solids and sold as high-protein animal feed.

Following distillation, oil may be separated from the stillage by an oil separation step or phase. The non-alcohol stream discharged from the distillation system can be fed to a separation phase to separate stillage from the wet grain. An oil separation step may utilize any technology used to separate stillage into a lipid rich phase and into one or more streams. Stillage can be separated into a lipid rich phase, an aqueous phase, and a solid phase. The oil separation step may include a mechanical separation means to divide materials based on differences in density and size. The mechanical separation means may include decanting vessels, centrifuges, filters, or a combination thereof. In addition, more than one type of mechanical separation means may be used.

The mechanical means may be continuous, semi-continuous, or batch operated. In one embodiment, the mechanical means may be used to divide the stillage into at least one outlet stream. In addition, one or more mechanical means may be used in series or in parallel to separate the lipid rich phase, the aqueous phase, and the solid phase. If using one or more mechanical means, resulting streams may be recombined.

Centrifuges that may be used include decanter centrifuges, disc stack centrifuges, basket centrifuges, tubular centrifuges, auto-desludging centrifuges, nozzle centrifuges, solid disk decanters.

Figure 2:
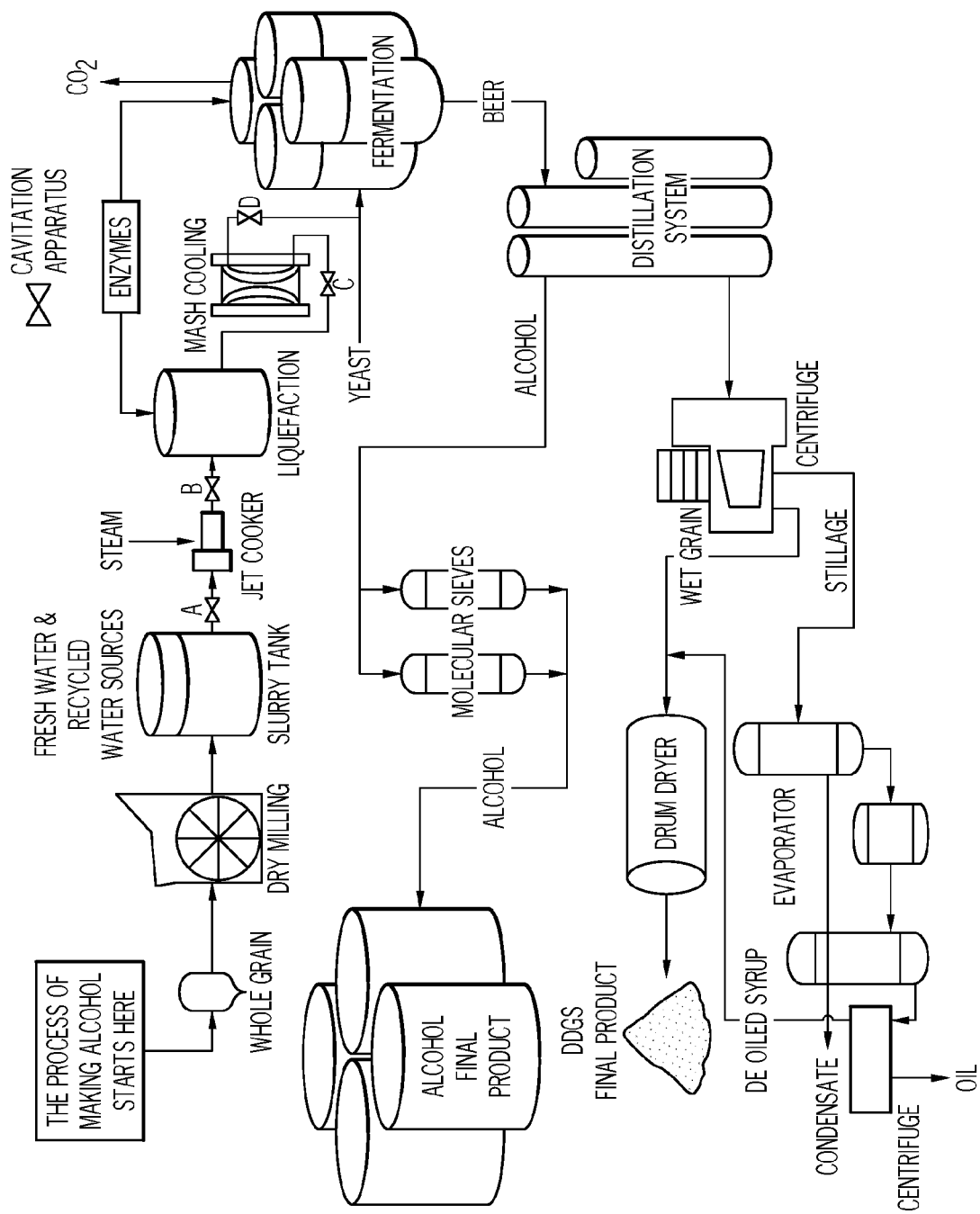
FIG. 2 is a process flow diagram of an alcohol production process and an oil by-product process utilizing cavitation energy being applied upstream of the distillation phase.

As shown in FIG. 2, four locations, A through D, for utilizing a cavitation apparatus to provide cavitation energy to the grain-based liquid stream prior to distillation are identified. One cavitation apparatus can be located solely at one of the locations such that only one cavitation apparatus is used in the alcohol production process. Alternatively, one or more cavitation apparatuses can be used at each or multiple locations or combinations thereof to provide a multi-cavitation system for enhancing by-product oil yield in an alcohol production process.

As shown, the grain-based liquid stream can exit the slurry tank and be passed through a cavitation apparatus, such as a controlled-flow cavitation apparatus, labeled as location A, which is used to apply cavitation energy to the grain-based liquid stream upstream of the heating phase shown as a jet cooker in FIG. 2. At location A, prior to the heating phase, the grain-based liquid stream can be at a temperature in the range of 20 to 85 degrees Celsius, and preferably at an ambient temperature in the range of 60 to 80 degrees Celsius. The grain-based liquid stream is passed through the cavitation apparatus at location A at a differential processing pressure of at least 150, 220, 500, 800 or 1,200 kPa such that there is a pressure drop across the cavitation apparatus of at least 150, 220, 500, 800 or 1,200 kPa wherein the upstream processing pressure is greater than 150, 220, 500, 800 or 1,200 kPa, such as in the range of 150 kPa to 11,000 kPa, 220 kPa to 11,000 kPa or 1,200 kPa to 11,000 kPa. Conventional high pressure pumps can be used to generate sufficient upstream processing pressures to accommodate the pressure needed to force or pass the grain-based liquid stream through the cavitation apparatus and the specified preferred differential processing pressure. The differential processing pressure and pressure drop across the cavitation apparatus can be in the range of 150 kPa to 11,000 kPa, 220 kPa to 11,000 kPa or 1,200 kPa to 11,000 kPa.

After passing through the controlled flow cavitation apparatus at location A, the grain-based liquid stream may pass through the heating phase to heat and hold the grain-based liquid stream at an elevated temperature as known in an alcohol production process. For example, a jet cooker may heat the grain-based liquid stream to a temperature in the range of 50 to 100 degrees Celsius. As shown, the jet cooker heating phase is the only heating phase prior to the distillation phase of the alcohol production process shown in FIG. 2.

In another embodiment, the grain-based liquid stream can pass through a cavitation apparatus at location B to apply cavitation energy to the stream, wherein location B is downstream or after the heating phase shown as a jet cooker. Location B for the cavitation apparatus is also upstream or prior to the liquefaction phase in which enzymes can be added to the grain-based liquid stream to promote breakdown of starches in the stream. Subsequent to the heating phase, the grain-based liquid stream can be at a temperature in the range of 50 to 100 degrees Celsius at location B, and preferably at 80 to 100 degrees Celsius. The grain-based liquid stream is passed through the cavitation apparatus at location B at a differential processing pressure of at least 150, 220, 500, 800 or 1,200 kPa such that there is a pressure drop across the cavitation apparatus of at least 150, 220, 500, 800 or 1,200 kPa. The differential processing pressure and pressure drop across the cavitation apparatus can be in the range of 150 kPa to 11,000 kPa, 220 kPa to 11,000 kPa or 1,200 kPa to 11,000 kPa. Before entering the cavitation apparatus at location B, the grain-based liquid stream may be held at the elevated temperature of 80 to 100 degrees Celsius for a period of 4 to 8 hours. Exiting the controlled flow cavitation apparatus at location B, the grain-based liquid stream is at a temperature in the range of 50 to 100 degrees Celsius.

In another embodiment, following the liquefaction phase and enzyme addition and prior to entering the cooling phase, for instance, the mash cooling phase, the grain-based liquid stream including enzymes can be passed through a cavitation apparatus at location C. Enzymes included in the grain-based liquid stream can include amylase, α-amylase, β-amylase, and γ-amylase, protease, cellulase, xylanases, ligninases enzymes or combinations thereof. Cavitation energy is applied to the grain-based liquid medium at a temperature in the range of 50 to 100 degrees Celsius, and preferably 60 to 90 degrees Celsius directly upstream of the cooling phase. The grain-based liquid stream is passed through the cavitation apparatus at location C at a differential processing pressure of at least 150, 220, 500, 800 or 1,200 kPa such that there is a pressure drop across the cavitation apparatus of at least 150, 220, 500, 800 or 1,200 kPa. The differential processing pressure and pressure drop across the cavitation apparatus can be in the range of 150 kPa to 11,000 kPa, 220 kPa to 11,000 kPa or 1,200 kPa to 11,000 kPa.

During the mash cooling phase, enzymes break starch polymers of the grain into shorter sections of sugar and create the sugar mash. As shown, the mash cooling phase is the only cooling phase prior to distillation in the alcohol production process shown in FIG. 2. After exiting the mash cooling phase, the grain-based liquid stream exits at a temperature at or below 55 degrees Celsius, preferably at a temperature in the range of 30 to 55 degrees Celsius. The grain-based liquid stream at location C can further include enzymes that are added during the liquefaction phase and before the cooling phase. The concentration of the enzymes in the grain-based liquid stream at point C can be 1 weight percent or less or as known in the art. The cooling phase lowers the temperature of the grain-based liquid stream to a temperature in the range of 20 to 55 degrees Celsius.

In another embodiment, the grain-based liquid stream can be passed through a cavitation apparatus at location D. Location D is downstream of the cooling phase and prior to the fermentation and distillation phases of the alcohol production process of FIG. 2. Cavitation energy is applied to the grain-based liquid medium at location D at a temperature in the range of 20 to 55 degrees Celsius, and preferably 20 to 40 degrees Celsius. As noted above with regard to the other cavitation locations, the grain-based liquid stream is passed through the cavitation apparatus at location D at a differential processing pressure of at least 150, 220, 500, 800 or 1,200 kPa such that there is a pressure drop across the cavitation apparatus of at least 150, 220, 500, 800 or 1,200 kPa. The differential processing pressure and pressure drop across the cavitation apparatus can be in the range of 150 kPa to 11,000 kPa, 220 kPa to 11,000 kPa or 1,200 kPa to 11,000 kPa.

The grain-based liquid stream at location D can also include enzymes, either cellulase or non-cellulase or a combination of both as noted above. The total content of the enzymes in the grain-based liquid stream at location D is 2 weight percent or less. The grain-based liquid stream at location D can also include yeast that is added to convert sugars present in the stream to carbon dioxide and alcohol. Yeast is present at a conventional weight percent as known in the art.

Use of a cavitation apparatus at locations A through D, or combinations thereof, can increase by-product oil yield from grain in the range of 5 to 35 percent as compared an alcohol product process that does not use cavitation energy or apply it prior to the distillation phase. In an undesirable manner, the use of cavitation energy to process a stream of an alcohol production process after distillation or fermentation phases can create microemulsions that entrap free oil and make it difficult and expensive to separate as compared to the described method herein. It is believed that the use of cavitational energy downstream of the distillation and fermentation phases does not increase by-product oil yield at the level that results from practicing the described methods herein.

The cavitation apparatus used herein at locations A through D can be a static or dynamic cavitation apparatus. Examples of static cavitational energy sources that can be used to apply cavitational energy include, but are not limited to, static mixers, orifice plates, perforated plates, nozzles, venturis, jet mixers, eductors, cyclonettes (e.g., Fluid-Quip, Inc.), and control flow cavitation apparatuses (e.g., Arisdyne systems, Inc.), such as those described in U.S. Pat. Nos. 5,810,052; 5,931,771; 5,937,906; 5,971,601; 6,012,492; 6,502,979; 6,802,639; 6,857,774 and 7,667,082, the entire contents of which are incorporated herein by reference. Differential processing pressure for use with static cavitation apparatuses can be in the range of at least 220 kPa and 220 kPa to 11,000 kPa or 1,200 kPa to 11,000 kPa. Additionally, dynamic cavitational energy sources, such as those with moving parts, that can be used include, but are not limited to, rotary milling devices (e.g., EdeniQ Cellunator™), rotary mixers (e.g., HydroDynamics SPR, Magellan™), rotor-rotor (e.g., Eco-Fusion Canada Inc.) and rotor-stator devices (e.g., IKA® Works, Inc., Charles Ross & Son Company, Silverson Machines, Inc., Kinematica Inc.), such as those described in U.S. Pat. Nos. 6,857,774; 7,178,975; 5,183,513; 5,184,576; 5,239,948; 5,385,298; 5,957,122; and 5,188,090. Differential processing pressure for use with static cavitation apparatuses can be in the range of at least 150 kPa and 150 kPa to 11,000 kPa or 1,200 kPa to 11,000 kPa.

It should now be apparent that there has been provided, in accordance with the present invention, a novel process for enhancing enzyme activity in grain-based liquid medium that satisfies the benefits and advantages set forth above. Moreover, it will be apparent to those skilled in the art that many modifications, variations, substitutions and equivalents for the features described above may be effected without departing from the spirit and scope of the invention. Accordingly, it is expressly intended that all such modifications, variations, substitutions and equivalents which fall within the spirit and scope of the invention as defined in the appended claims to be embraced thereby.

The preferred embodiments have been described, herein. It will be apparent to those skilled in the art that the above methods may incorporate changes and modifications without departing from the general scope of this invention. It is intended to include all such modifications and alterations in so far as they come within the scope of the appended claims or the equivalents thereof.

What is claimed is:

1. A method for enhancing by-product oil yield from an alcohol production process comprising:
   passing a grain-based liquid stream containing entrapped oil of the alcohol production process through a cavitation apparatus to apply a cavitation energy with sufficient differential processing pressure to the grain-based liquid stream to break or fracture protein and fiber matrix contained in the grain-based liquid stream to release the entrapped oil by disaggregating the entrapped oil in the grain-based liquid stream, wherein the cavitation energy is applied to the grain-based liquid stream containing entrapped oil prior to a fermentation phase of the alcohol production process,
   separating oil from stillage following an alcohol distillation phase such that the by-product oil yield is improved by at least 10 percent as compared to the oil yield from an alcohol production process without the cavitational energy being applied prior to the fermentation phase.

2. The method of claim 1, wherein the cavitation energy is produced by static cavitation means or dynamic cavitation means.

3. The method of claim 1, wherein the differential processing pressure in the range of 150 kPa to 11,000 kPa.

4. The method of claim 1, wherein grain-based liquid stream is produced using a dry grind or modified dry grind process.

5. The method of claim 1, wherein the grain-based liquid stream further comprises and enzyme selected from the group consisting of amylase, α-amylase, β-amylase, and γ-amylase, protease, cellulase, xylanases, ligninases or combinations thereof.

6. The method of claim 1, wherein the grain-based liquid stream is at a temperature in the range of 20 to 85 degrees Celsius and the cavitation energy is applied prior to the grain-based liquid stream entering a heating phase of the alcohol production process.

7. The method of claim 1, wherein the grain-based liquid stream is at a temperature in the range of 50 to 100 degrees Celsius and the cavitation energy is applied after the grain-based liquid stream is heated in the alcohol production process.

8. The method of claim 7, wherein the grain-based liquid stream further comprises an enzyme and the cavitation energy is applied prior to a cooling phase of the alcohol production process.

9. The method of claim 1, wherein the grain-based liquid stream is at a temperature in the range of 20 to 55 degrees Celsius and the cavitation energy is applied after the grain-based liquid stream is cooled in the alcohol production process.

* * * * *